United States Patent [19]
Kummer et al.

[11] Patent Number: 5,516,335
[45] Date of Patent: May 14, 1996

[54] INTRAMEDULLARY NAIL FOR FEMORAL LENGTHENING

[75] Inventors: Frederick Kummer; Victor Frankel, both of New York, N.Y.

[73] Assignee: Hospital for Joint Diseases Orthopaedic Institute, New York, N.Y.

[21] Appl. No.: 36,419

[22] Filed: Mar. 24, 1993

[51] Int. Cl.⁶ .................................................. A61B 17/72
[52] U.S. Cl. ................................................ 606/63; 606/64
[58] Field of Search .................................. 606/62, 63, 64, 606/67, 68; 411/469, 397, 396

[56] References Cited

U.S. PATENT DOCUMENTS

| | | |
|---|---|---|
| 2,672,861 | 3/1954 | Jonas et al. . |
| 3,530,854 | 9/1970 | Kearney . |
| 4,204,531 | 5/1980 | Aginsky . |
| 4,467,794 | 8/1984 | Maffei et al. . |
| 4,516,569 | 5/1985 | Evans et al. . |
| 4,520,511 | 6/1985 | Gianezio et al. . |
| 4,628,920 | 12/1986 | Mathys, Jr. et al. . |
| 4,733,654 | 3/1988 | Marino . |
| 4,805,607 | 2/1989 | Engelhardt et al. . |
| 4,946,459 | 8/1990 | Bradshaw et al. . |
| 5,112,333 | 5/1992 | Fixel . |
| 5,122,141 | 6/1992 | Simpson et al. . |

*Primary Examiner*—Tamara L. Graysay
*Attorney, Agent, or Firm*—Stephen E. Feldman

[57] ABSTRACT

An intramedullary nail for the lengthening of bones. It comprises base and extension means and adjustment and rectilinear means. The base means includes an elongated means having a longitudinal axis, and axial opening therethrough and having an inner surface, and distal and proximal ends. The adjustment means has an axis, an outer surface, and is disposed within the distal end of the base means. The rectilinear means are formed on the inner and outer surfaces of the axial opening of the base means and the adjustment means, respectively, for permitting rectilinear motion of the adjustment means toward the proximal end of the base means. The extension means has an axis, and is telescopically disposed within the proximal end of the base means; it is affixed to the adjustment means.

31 Claims, 3 Drawing Sheets

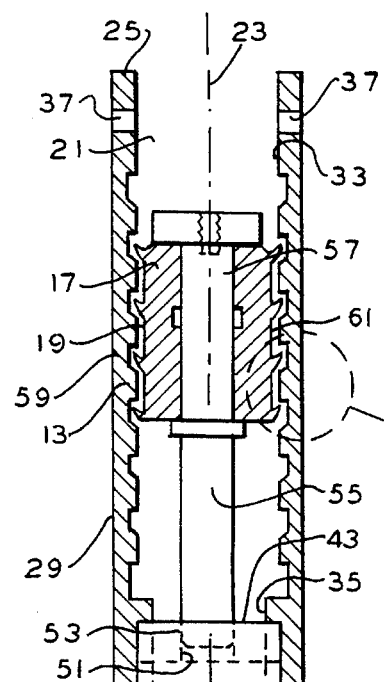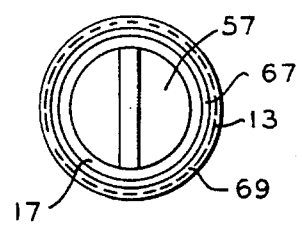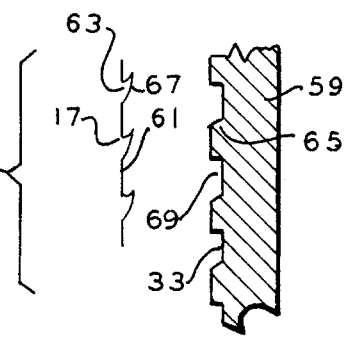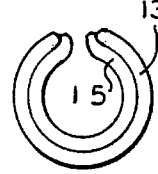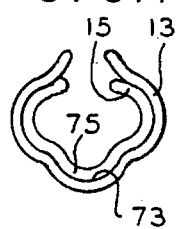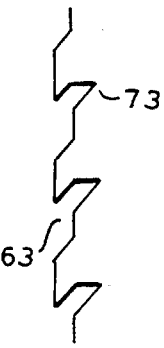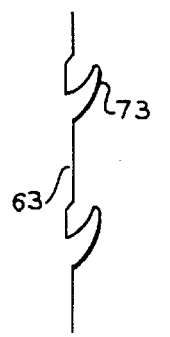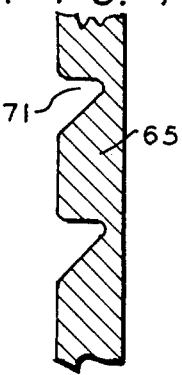

INTRAMEDULLARY NAIL FOR FEMORAL LENGTHENING

FIELD OF THE INVENTION

This invention relates to the field of bone fixation devices and in particular to an intramedullary nail which can be used for lengthening femoral bones.

BACKGROUND OF THE INVENTION

The use of various fastening devices for rejoining bones which have become fractured is well-known. A common example of the same is the "locked" nail which comprises a predetermined length of rod having apertures for transverse locking screws at both ends. Another example is modular nails which comprise a pair of interlocking tubular members adapted to be inserted in the intramedullary passages of the parts of a fractured bone; they are quite expensive, but do reduce the number of devices required to fit all patients. Another intramedullary nail device includes an extended tubular shaft having a predetermined cross-section having transverse apertures at various locations along its length. Such a device is inserted into an intramedullary cavity of a bone and secured within the bone by transverse bone screws placed through an aligned aperture in the device.

An intramedullary device which can be adjusted in length after installation, is disclosed by Bradshaw in U.S. Pat. No. 4,946,459. This intramedullary device comprises, a slotted nail member which extends toward the distal end of the bone, and is affixed at the distal end by means of pins or screws extending through the bone. At the proximal end of the nail is an interiorly spliced receptacle affixed to the end of the nail. The spliced receptacle has an interior shoulder therein approximately mid-way of its length. An exteriorly spliced adjustment shaft is adapted to fit into the spliced receptacle and to bear against the shoulder thereof. The shaft is mounted within an elongated cylinder having an interiorly spliced end cap at its distal end whereby the shaft is free to slide within the cylinder but is restrained from rotation with respect thereto. The interior of the cylinder is threaded over a major portion of its length from the proximal end toward the spliced end cap. The proximal end of the shaft has a stop collar mounted thereon to prevent the shaft from sliding out of the cylinder through the end cap, but to permit insertion and removal of the shaft through the proximal end of the cylinder. An adjustment screw is threaded into the threaded cylinder and is adapted to bear against the stop collar. The screw has a socket, such as a hexagonal Allen socket, in its proximal end to permit driving the screw into the cylinder, and hence driving the spliced shaft toward the distal end of the bone, which in turn drives the nail toward the distal end away from the cylinder. A cylindrical end cap having external threads thereon is threaded into the cylinder after the adjusting screw has been inserted therein. Mounted to the end cap extending therefrom is a longitudinal section of biocompatible tubing. Such devices, however require transcutaneous adjustment to achieve lengthening.

SUMMARY OF THE INVENTION

The present invention, in its broadest aspect, is directed to an intramedullary nail for the lengthening of bones. It comprises base and extension means and adjustment and rectilinear means. The base means includes an elongated means having a longitudinal axis, an axial opening therethrough, and having an inner surface, and distal and proximal ends. The adjustment means has an axis, an outer surface, and is disposed within the distal end of said base member. The rectilinear means are formed on a said inner and outer surfaces of said axial opening of said base means and said adjustment means, respectively, for permitting rectilinear motion of the adjustment means toward said proximal end of said base means. The extension means has a axis, and is telescopically disposed within the proximal end of said base means; it is affixed to said adjustment means.

In a narrower aspect, one embodiment of the present invention is directed to an intramedullary nail for the lengthening of bones. It essentially comprises base and extension means, a plunger, and ratchet and holding pawl means. The base means is an elongated, cylindrical, metal member having a longitudinal axis, an axial opening therethrough, an inner surface, and distal and proximal ends. The plunger has a cylindrical shape, an axis and an outer surface; it is disposed within the distal end of said base means. The ratchet means is formed on the outer surface of said plunger and is made of a resilient material. The holding pawl means is formed on the inner surface of said base means, and it comprises a plurality of slots extending axially along said inner surface. The ratchet and pawl permits unidirectional rectilinear motion to said plunger towards said proximal end of said base means. The extension means is a cylindrical member having an axis and is telescopically mounted within the proximal end of said base means and is in frictional engagement therewith as well as being axially aligned with one another. The nail further includes a rod means fixedly connected at one end to said plunger and at another end to said inner end of said extension means. The base means has upper portions mounting said plunger and a radially, inwardly extending flange having a central aperture. The flange is disposed between said upper and lower portions of said base means and is adapted to overlie the inner end of said extension means. The base and extension means include groove and key means disposed between them for preventing their relative rotational motion with respect to one another. Furthermore, transversal bores, all formed in the outer ends of said base and extension means, respectively, allow the passage of a fixation pin through each bore to affix the base and extension means to the bone.

In a narrower aspect, the preferred embodiment has its pawl means comprising a single split ring, disposed within a slot in the base member. Alternately, the ratchet means comprises a plurality of sector members having radial, outwardly extending, peripheral shoulders for engaging the bore in the split ring.

Also, in its narrowest aspect, another embodiment has its ratchet means comprising a plurality of teeth, extending axially along the outer surface of said plunger means.

Furthermore, in its narrowest aspect, still another embodiment has its ratchet means comprising opposing arms disposed within said plunger means, which arms are coupled together at one end to permit radial pivoting; spring bias means are connected between their other ends to bias their free end radially outward to engage said pawl.

Since various embodiments of the invention have parts in common, like reference numerals are used to indicate like elements.

BRIEF DESCRIPTION OF THE DRAWINGS

FIG. 5A is a simplified diagrammatic front elevational view, with the plunger and base members shown in cross-section, of another embodiment of the inventive intramedullary nail;

FIG. 5B is a top end elevation view of the nail of FIG. 5;

FIG. 6A is a sectional end view of just the base and extension members of the nail of FIG. 5;

FIG. 6B is a sectional view of the base and extension members of FIG. 6A at their keying sections;

FIG. 7A is an enlarged fragmentary side sectional view of the ratchet-pawl mechanism portion of the nail of FIG. 5;

FIG. 7B is an enlarged fragmentary side sectional view of another embodiment of the pawl means of the nail of FIG. 5;

FIGS. 7C and 7D are enlarged fragmentary side views of additional embodiments of the ratchet means of the nail of FIG. 5;

DETAILED DESCRIPTION OF THE INVENTION

Figure 2:
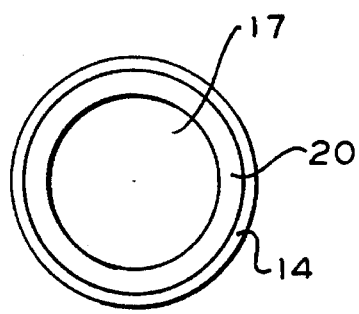
FIG. 2 is a top end elevation view of the nail of FIG. 1.
Figure 3:
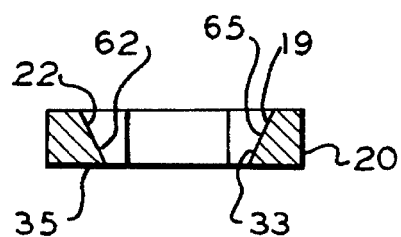
FIG. 3 is a sectional side view of the split ring of the nail of FIG. 1.
Figure 4:
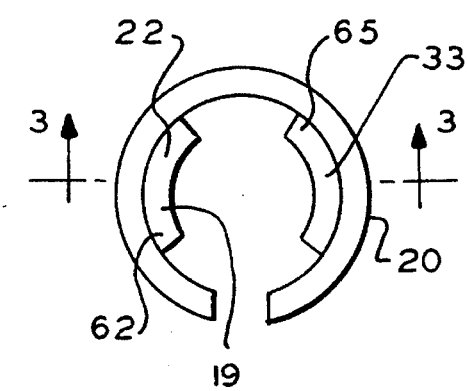
FIG. 4 is a top end elevation view of the split ring of FIG. 3.
Figure 1:
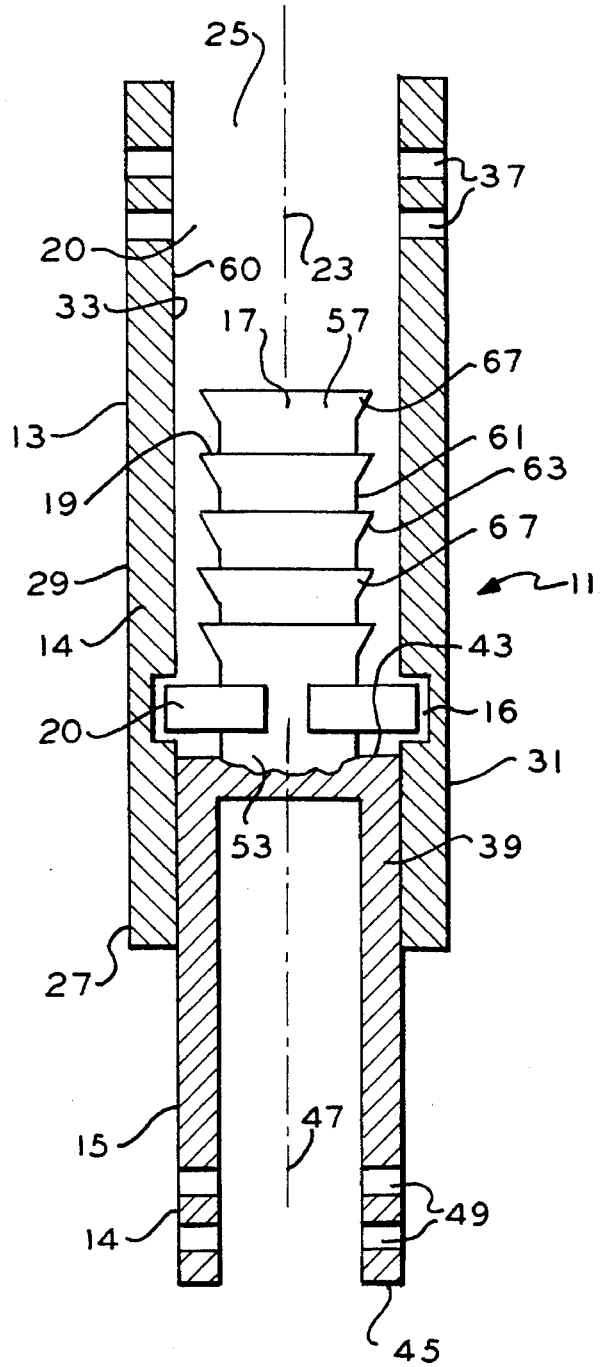
FIG. 1 is a simplified diagrammatic front elevation view, with the base and extension members shown in cross-section, of the preferred embodiment of the inventive intramedullary nail.

Referring specifically to FIGS. 1–4, the preferred embodiment of the improved intramedullary nail for the lengthening of bones and more specifically for femoral lengthening, is generally designated by reference numeral 11. It essentially comprises an elongated, generally cylindrical, base means 13, an elongated, tubular, extension means or member 15, a generally cylindrical adjustment means or plunger 17, disposed within the base means 13, and rectilinear means 19 formed on the surface(s) of the base means and plunger, 13 and 17, respectively. The base means 13 comprises an elongated, cylindrical, base member 14 having a slot 16 circumferentially extending around its inner surface 33, and a split ring 20 fixed within said slot 16. The split ring 20 has a bore 22 in the form of a truncated conical section. The base member 14 has an axial opening 21 therethrough, a longitudinal axis 23, distal and proximal ends, 25 and 27, respectively, and upper and lower portions, 29 and 31, respectively. Transversal bores 37 are formed at the distal end 25 of the base member 14 to permit the passage therethrough of fixation pins (not shown). The extension member 15 has upper and lower portions, 39 and 41, respectively, completely closed and completely open inner and outer or distal ends, 43 and 45, respectively, and a longitudinal axis 47. The extension member 15 has its upper portion 39 telescopically mounted through the proximate end 27 and in the lower portion 31 of the base member 14. Additionally, the extension member 15 is mounted in frictional engagement with the base member 14, and their axes 23 and 47 are aligned with one another. The lower surface 35 of the split ring 20 of the base means 13 overlies the inner end of the extension member 15 and serves to limit its inward travel. Transversal bores 49 are similarly formed at the outer or distal end of the extension member 15 to permit the passage therethrough of fixation pins (not shown). The plunger 17 is shown axially mounted within bore 22 of split ring 20 as well as being disposed within a central-upper portion 59 of the opening 21 in the base member 14 for axial movement within said bore and opening, 22 and 21, respectively, toward its proximate end 27. The plunger 17 is rigidly fixed to the inner end of extension member 15 through a short rod member 55. The outer surface 61 of the plunger 17 engages the inner surface 33 of the base means 13, and the form of engagement is described hereinafter. The inner surface 33 of the base means 13 comprises the inner surface 60 of the base member 14 and/or the inner surface 62 of the split ring 20.

The rectilinear means 19 comprise ratchet means or ratchet 63 and pawl means or pawl 65 formed on the inner surface 62 defining the bore opening 22 in the split ring 20 of base means 13 (FIG. 3) and on the outer surface 61 of the plunger 17, respectively. The pawl 65 is in the form of a holding pawl allowing movement in only one direction. The ratchet 63 and pawl 65 forms a ratchet and pawl mechanism which permits unidirectional axial movement of the plunger 17 toward the proximal end 27 of the base member 13.

Figure 8:
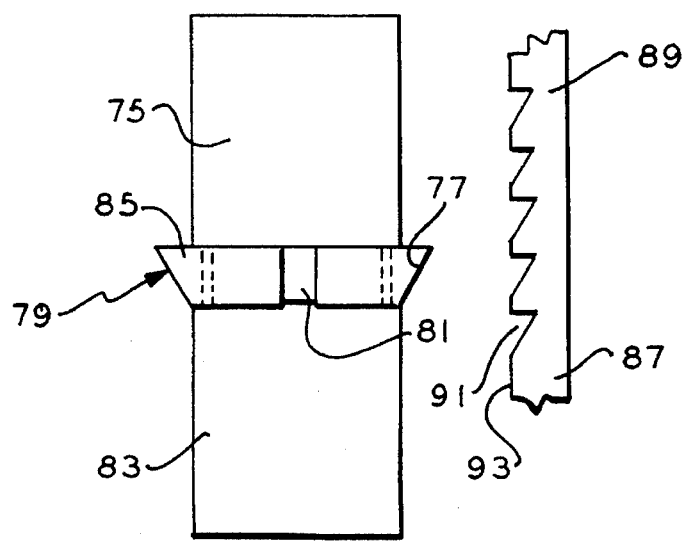
FIG. 8 is an enlarged front elevation of the plunger and ratchet elements and a side sectional view of the pawl means of another embodiment of nail of FIG. 5.

The preferred embodiment of the invention as shown in FIGS. 1–4, utilize a plunger 17 which can be made entirely of the same material such as polyethylene or made of a different material. In the former instance, the ratchet 63 would be made of the same material since it is integral with the plunger 17. In the later instance, the embodiment shown in FIG. 8 illustrates the same; the plunger 75 being in the form of a hollow metal cylindrical rod and a ratchet 77 in the form of a plastic split ring 79. The base member or pawl means 87 of the base means 89 is preferably made of a metallic material as preferably would the extension member 15; however the split ring 79 is preferably made of a plastic material. The lower portion 31 of the base member 14 (FIG. 1), which extends from the lower end of the slot 16 to the proximate end 27, must be of sufficient length (i.e. 2 cm) to provide adequate support to the extension member 15 when it is disposed in its extended position.

Referring specifically to FIGS. 5A and 5B, another embodiment of the intramedullary nail for the lengthening of bones is also generally designated by reference numeral 11. It essentially comprises an elongated, cylindrical, base means or base member 13, an elongated, tubular, extension member means or extension member 15, a cylindrical adjustment means or plunger 17, disposed within the base member 13, and rectilinear means 19 formed on the surfaces of the base member and plunger 13 and 17, respectively. The base member 13 has an axial opening 21 therethrough, a longitudinal axis 23, distal and proximal ends, 25 and 27, respectively, upper and lower portions, 29 and 31, respectively, and an inner surface 33. A radially inward extending flange 35 having a central aperture 36, is disposed between the upper and lower portions, 29 and 31, respectively. Transversal bores 37 are formed at the distal end 25 of the base member 13 to permit the passage therethrough of fixation pins (not shown). The extension member 15 has upper and lower portions, 39 and 41, respectively, partially and completely closed inner end and outer or distal ends, 43 and 45, respectively, and a longitudinal axis 47. The extension member 15 has its upper portion 39 telescopically mounted through the proximate end 27 and in the lower portion 31 of the base member 13. Additionally, the extension member 15 is mounted in frictional engagement with the base member 13, and their axes 23 and 47 are aligned with one another. The flange 35 on the base member 13 overlies the inner end 43 of the extension member 15 and serves to limit its inward travel. Transversal bores 49 are similarly formed at the outer or distal end of the extension 15 to permit the passage therethrough of fixation pins (not shown). A central aperture 51 having internal screw threads is formed in the inner end 43 of the extension member 15 and fixedly connects with screw threads formed on the inner end 53 of a rigid rod 55, which has its screw head outer end 57 connected through and to the plunger 17. The plunger 17 is axially mounted on the outer end 57 of the rod 55 and is disposed within a central-upper portion 59 of the opening 21 in the base member 13 for axial movement therein toward its proximate end 27. The outer surface 61 of the plunger 17 engages the inner surface 33 of the base member 13, and the form of engagement is described hereinafter.

The rectilinear means 19 comprise ratchet means or ratchet 63 and pawl means or pawl 65 formed on the inner surface 33 defining the axial opening 24 in the base member 13 and on the outer surface 61 of the plunger 17, respectively. The pawl 65 is in the form of a holding pawl allowing movement in only one direction. The ratchet 63 and pawl 65 forms a ratchet and pawl mechanism which permits unidirectional axial movement of the plunger 17 toward the proximal end 27 of the base member 13. The embodiment shown in FIG. 5 utilizes a plunger 17 which is entirely made of a resilient material composed of polyethylene. Accordingly the ratchet 63 is made of the same material since it is integral with the plunger 17. The base member 13 is preferably made of a metallic material; accordingly the pawl 65 is made of the same material since, it too, is integral with the base member 13. Referring now to FIGS. 6A and 6B, the base and extension members 13 and 15, respectively, are shown as including groove and key means, 66 and 68, respectively. Referring specifically to FIG. 5B and FIG. 7A, the ratchet 63 comprises a plurality of upstanding, spaced apart, resilient teeth 67 extending both axially and radially along the outer surface 61 of the plunger 17. The pawl 65 comprises a plurality of rigid slots or grooves 69 which extend radially outward. Such grooves 69 are preferably no greater than 0.25 mm and their pitch is either 0.5 or 1.0 mm. FIG. 7B illustrates an alternative version wherein the grooves 71 of pawl 65 are shown as triangular shaped. FIG. 7C illustrates a ratchet 63' having upstanding, straight, teeth 73', which preferably have a radial height of between 0.05 to 0.15 mm. FIG. 7D illustrates a ratchet 63" having upstanding, curved, teeth 73".

Referring now to FIG. 8, this embodiment of the invention comprises a plunger 75 in the form of a hollow cylindrical rod and a ratchet 77 in the form of a split ring or sector means 79 disposed in an annular slot 81 formed on the outer surface 83 of the plunger 75. The split ring 79 radially extends around the outer surface 83 of the plunger 75. Outwardly extending, peripheral, shoulders 85 engage pawl means 87 on a tubular cylindrical base means 89 (only a portion of which is shown). These pawl means 87 are in the form of triangularly shaped slots 91 formed in the inner surface 93 of the base means 89; the slots 91 extend both axially and radially along the inner surface 93 of the base means 89, and retain the plunger 75 in place, axially, within the base means 89.

Figure 9A:
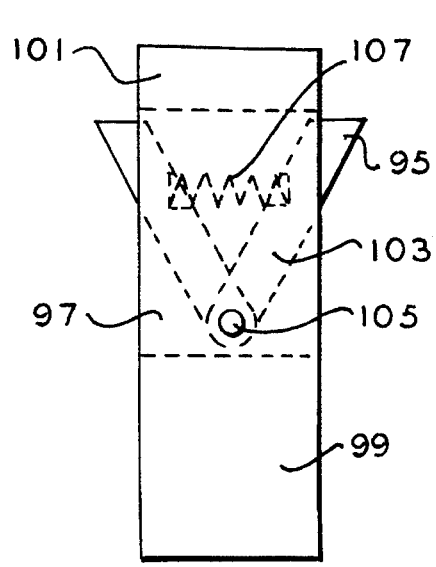
FIGS. 9A and 9B are enlarged front and side elevational views of the plunger and ratchet elements of another embodiment of the nail of FIG. 5.
Figure 9B:
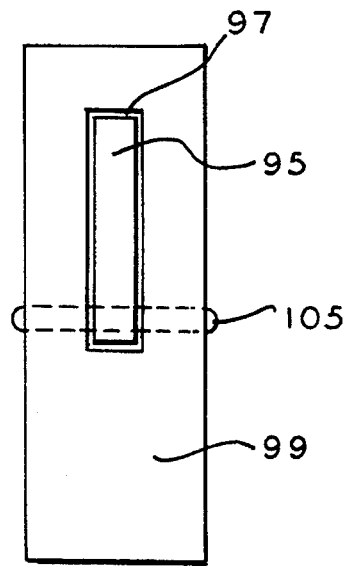

Referring to FIGS. 9A and 9B, still another embodiment of a ratchet 95 is shown connected within a slot 97 formed in a plunger 99 in the form of a hollow cylindrical rod 101. The ratchet 95 comprises a pair of opposing arms 103 pined together at one end by a pin 105, having a spring 107 connected between their free ends to bias them radially outward to engage their associated pawl (not shown).

In operation, referring to the preferred embodiment shown in FIGS. 1–4, after the nail 11 is installed in a patient's femur as described hereinafter, when the extension member 15 is moved downward and away from the base member 13, the plunger or adjustment member 17 axially moves into the bore 22 of the split ring 20 until the teeth 67 of the first or lowermost ratchet portion 63 thereof engage the inner surface 62 of the split ring 20. In order to move the extension member 15 any further downward, sufficient force must be applied thereto for a sufficient time to open the split ring 20 sufficiently to permit at least the first ratchet portion 63 to pass through the bore 22 of the split ring 20. The required amount of a force necessary to increment the plunger 17 one level is a function of the resilience of the material which form the split ring 20 and the vesilience of the teeth 67 of the ratchet portion 63. Since the split ring 20 permits the ratchet 63 to move in only one direction, downward, the split ring 20 functions as a holding pawl. Since the other embodiments of the invention operate in a manner substantially similar to the embodiment described above, the manner of operation thereof is not provided.

The previously described intramedullary nail 11 is utilized in essentially the same conventional manner as any other nail to repair a femur fracture. Such conventional method comprises the standard trochanteric approach which first requires an incision to obtain access to the trochanter. Then the inner surface of the femur is reamed through the trochanter and within the intramedullary passage of the upper portion of the femur (to the diameter of the base element 13) up and to where the femur is to be cut; then the lower portion of the femur past the cut point is reamed to the diameter of the extension element 15. The femur is then completely cut through at the desired cut point by the use of an internal saw or through a small incision. The nail 11 is then inserted in the reamed intramedullary passage at the cut point, the base and extension members, 13 and 15, respectively, being disposed within the upper and lower portions of the femur. The nail 11 is then anchored in place by placing pins or screws through the bores 37 in the distal end 25 of the base element 13 and through the bores 49 in the extension element 15 in the lower portion of the femur. Later, after two to four days, controlled traction is applied at the foot; both force and displacement is used to lengthen the nail the desired amount per unit time.

While the invention has been shown in preferred and other embodiments thereof, numerous changes or modifications may occur to workers in the art without departure from the spirit and scope of the invention. For example, the adjustment means can be hollow or solid, the plunger means could be an integral part of the extension means, and the ratchet and pawl can be made of a resilient material or metal.

What is claimed is:

1. An adjustable intramedullary nail for the lengthening of a bone which after locking is adjusted by externally applied force on/to the bone, comprising:

an elongated base means having a longitudinal axis, an axial opening therethrough and having an inner surface and distal and proximal ends;

adjustment means having an axis, an outer surface and disposed within the distal end of said base means;

rectilinear means formed on said inner and outer surfaces of said axial opening of said base means and said adjustment means, respectively, for permitting controlled incremental rectilinear motion to said adjustment means by said externally applied force away from said distal end of said base means; and an extension means having an axis, and telescopically disposed within the proximal end of said base means, and affixed to said adjustment means.

2. The nail as recited in claim 1, wherein said base means is cylindrical in shape.

3. The nail as recited in claim 2, wherein said extension means is cylindrical in shape.

4. The nail as recited in claim 3, wherein said base means and extension means are axially aligned with one another.

5. The nail as recited in claim 4, wherein said base means and extension means include groove and key means disposed therebetween for preventing relative rotational motion between said base means and extension means.

6. The nail as recited in claim 1, wherein said rectilinear means is unidirectional.

7. The nail as recited in claim 1, wherein said base means comprises a base member and a split ring disposed within said base member.

8. The nail is recited in claim 7, wherein the rectilinear means comprise a pawl which is formed on the inner surface of said split ring.

9. An intramedullary nail for the lengthening of bones, comprising:

an elongated base means having a longitudinal axis, an axial opening therethrough and having an inner surface and distal and proximal ends;

adjustment means having an axis, an outer surface and disposed within the distal end of said base means;

rectilinear means formed on said inner and outer surfaces of said axial opening of said base means and said adjustment means, respectively, for permitting rectilinear motion to said adjustment means toward said proximal end of said base means; and an extension means having an axis, and telescopically disposed within the proximal end of said base means, and affixed to said adjustment means wherein said rectilinear means comprises a ratchet and pawl, the ratchet formed on one of said inner and outer surfaces of said base means and said adjustment means, respectively, and the pawl formed on the other said inner and outer surfaces of said base means and said adjustment means, respectively.

10. The nail as recited in claim 9, wherein said ratchet and pawl being formed of resilient and non-resilient materials, respectively.

11. The nail as recited in claim 10, wherein said resilient and non-resilient materials, comprise polymer and metal, respectively.

12. The nail as recited in claim 11, wherein said polymer comprises polyethylene.

13. The nail as recited in claim 9, wherein said base means and said adjustment means are formed of non-resilient and resilient materials, respectively.

14. The nail are recited in claim 9, wherein said ratchet and pawl being respectively formed on the outer and inner surfaces of said adjustment means and said base means, respectively.

15. The nails recited in claim 14, wherein said ratchet being formed of a resilient material.

16. The nail as recited in claim 14, wherein said pawl being formed of a non-resilient material.

17. The nail as recited in claim 9, wherein said adjustment means comprises a cylindrical shaped plunger.

18. The nail as recited in claim 9, wherein said pawl comprises a holding pawl.

19. The nail as recited in claim 9, wherein said pawl comprises a plurality of slots extending axially along the inner surface of said base means.

20. The nail as recited in claim 9, wherein said ratchet comprises a plurality of teeth extending axially along the outer surface of said adjustment means.

21. The nail as recited in claim 9, wherein said ratchet comprises at least one split ring radially extending around the outer surface of said adjustment means.

22. The nail as recited in claim 9, wherein said ratchet comprises at least one sector means having radial, outwardly extending, peripheral shoulders for retaining said adjustment means in place axially within said base means.

23. The nail as recited in claim 22, wherein said ratchet means comprises a plurality of sector members axially disposed along the outer surface of said plunger means.

24. The nail as recited in claim 9, wherein said ratchet comprises opposing arms disposed within said adjustment means and coupled together at one end to permit radial pivoting and bias means connected between their other ends to bias their other ends radially outward to engage said pawl.

25. An intramedullary nail for the lengthening of bones, comprising:

an elongated base means having a longitudinal axis, an axial opening therethrough and having an inner surface and distal and proximal ends;

adjustment means having an axis, an outer surface and disposed within the distal end of said base means;

rectilinear means formed on said inner and outer surfaces of said axial opening of said base means and said adjustment means, respectively, for permitting rectilinear motion to said adjustment means toward said proximal end of said base means; and an extension means having an axis, and telescopically disposed within the proximal end of said base means, and affixed to said adjustment means, wherein said base means has lower portions mounting said extension means in telescoping, frictional engagement therewith.

26. The nail as recited in claim 25, wherein said base means has upper portions mounting said adjustment means and radially inwardly extending flange having a central aperture, said flange disposed between said upper and lower portions of said base means and adapted to overlie the inner end of said extension means.

27. The nail as recited in claim 26, wherein said distal end of said base means and said outer end of said extension means each having a transversal bore to allow the passage of a fixation pin therethrough.

28. The nail as recited in claim 26, further including a rod means fixedly connected at one end to said adjustment means and at another end to said inner end of said extension means.

29. A modular intramedullary nail for the lengthening of bones, comprising:

an elongated, cylindrical, metal base means having a longitudinal axis, an axial opening therethrough, an inner surface, and distal and proximal ends;

a plunger having a cylindrical shape having an axis an outer surface, disposed within the distal end of said base means;

ratchet means disposed on the outer surface of said plunger;

holding pawl means formed on the inner surface of said base means, said pawl comprising a plurality of slots extending axially along said inner surface, said ratchet and pawl permitting unidirectional rectilinear motion to said plunger towards said proximal end of said base means;

a cylindrical extension means having an axis and mounted telescoping within the proximal end of said base means and in frictional engagement therewith and axially aligned with one another; and a rod means fixedly connected at one end to said plunger and at another end to said inner end of said extension means;

said base means having upper portions mounting said plunger and a radially, inwardly, extending flange having a central aperture, said flange being disposed between said upper and lower portions of said base means and adapted to overlie the inner end of said extension means;

said base means and extension means including groove key means disposed therebetween for preventing relative rotational motion between said base means and extension means, and transversal bores formed in the distal and outer ends of said base means, respectively, to allow the passage of a fixation pin through each bore.

30. The nail as recited in claim 29, wherein said ratchet means comprises at least one sector means having radial, outwardly extending, peripheral shoulders for retaining said plunger means in place axially within said base means.

31. The nail as recited in claim 29, wherein said ratchet means comprises opposing arms disposed within said plunger means and coupled together at one end to permit radial pivoting and bias means connected between their other ends to bias their other ends radially outward to engage said pawl.

* * * * *